US00PP33097P2

(12) United States Plant Patent
Van Swieten

(10) Patent No.: US PP33,097 P2
(45) Date of Patent: May 25, 2021

(54) ***PHALAENOPSIS* ORCHID PLANT NAMED 'PHALARALS'**

(50) Latin Name: ***Phalaenopsis* hybrid**
Varietal Denomination: PHALARALS

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,257

(22) Filed: Dec. 2, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALARALS', particularly characterized by light reddish-purple flowers with white centers and greenish-yellow-white lips, a concave flower shape in lateral view, apical lobes with reddish-purple lower surfaces, and is propagated by meristem tissue culture, is disclosed.

3 Drawing Sheets

Genus and species: *Phalaenopsis* hybrid.
Variety denomination: 'PHALARALS'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALARALS'.

The new *Phalaenopsis* plant is a product of a planned breeding program conducted by the inventor in Bleiswijk, the Netherlands. The objective of this breeding program was to create a new *Phalaenopsis* plant having light reddish-purple flowers with white centers and greenish-yellow-white lips, suitable for potted plant production.

The new *Phalaenopsis* plant 'PHALARALS' is a result of cross-pollination made by the inventor in November 2011 in Bleiswijk, the Netherlands, of the proprietary female, or seed parent, *Phalaenopsis* hybrid 'PHALVAPYH' (U.S. Plant Pat. No. 31,052) with the proprietary male, or pollen parent, *Phalaenopsis* hybrid '35337-02' (unpatented).

The new *Phalaenopsis* was selected by the inventor as a single plant within the progeny of the stated cross-pollination in a controlled greenhouse in Bleiswijk, the Netherlands, in August 2014. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 23, 2019 (Application no. 2019/2369), by Applicant who obtained the subject matter disclosed directly from the inventor. 'PHALARALS' has not been made publicly available or sold anywhere in the world prior to the effective filing date of this application with the exception of sales or disclosures made one year or less before the effective filing date of this claimed invention by Applicant who obtained 'PHALARALS' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALARALS' as a new and distinct variety of *Phalaenopsis* plant:

1) Light reddish-purple flowers with white centers and greenish-yellow-white lips;
2) Flower shape in lateral view is concave; and
3) Lower surface of apical lobe is reddish-purple.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in October 2020. Colors in the photographs may differ from the color values cited in the detailed botanical description, which accurately describe the actual colors of the new variety.

DESCRIPTION OF THE NEW VARIETY

Figure 1:
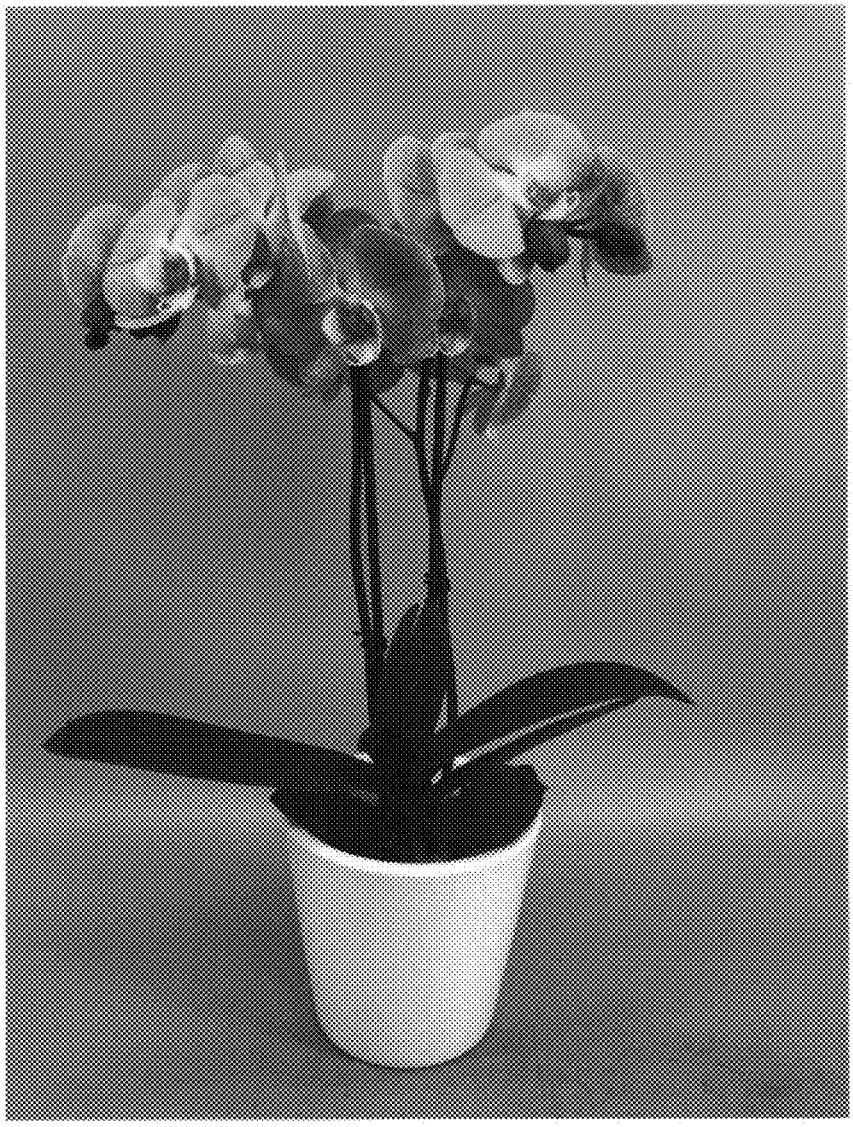
FIG. 1 shows the overall plant habit, including blooms, buds, and foliage of 'PHALARALS'.
Figure 2:
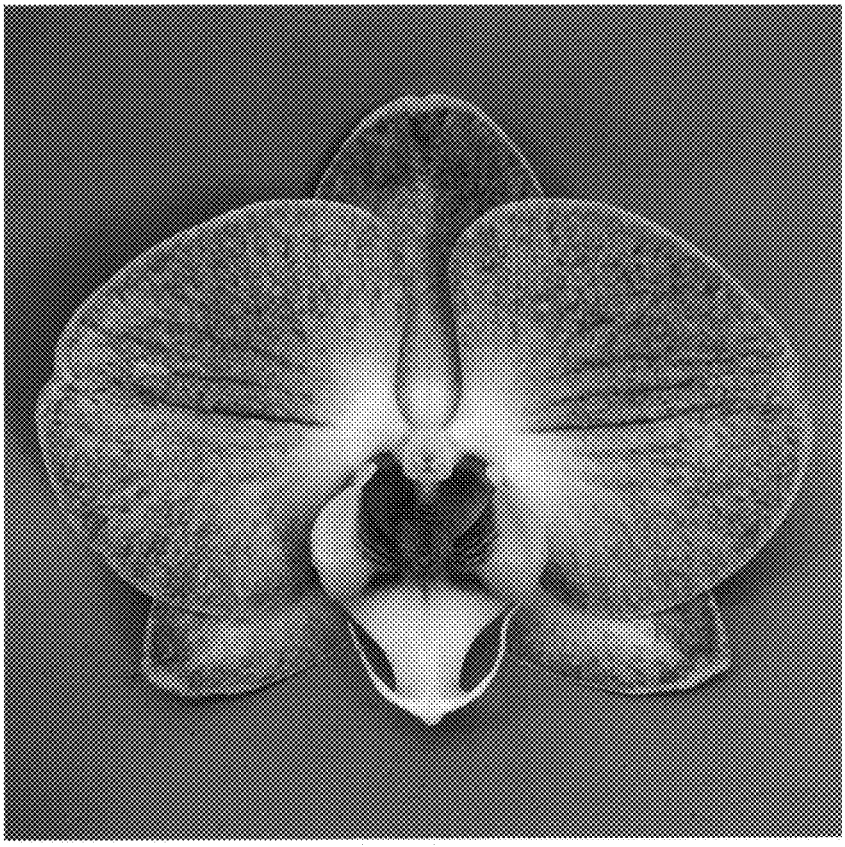
FIG. 2 shows a close-up of a flower of 'PHALARALS'.
Figure 3:
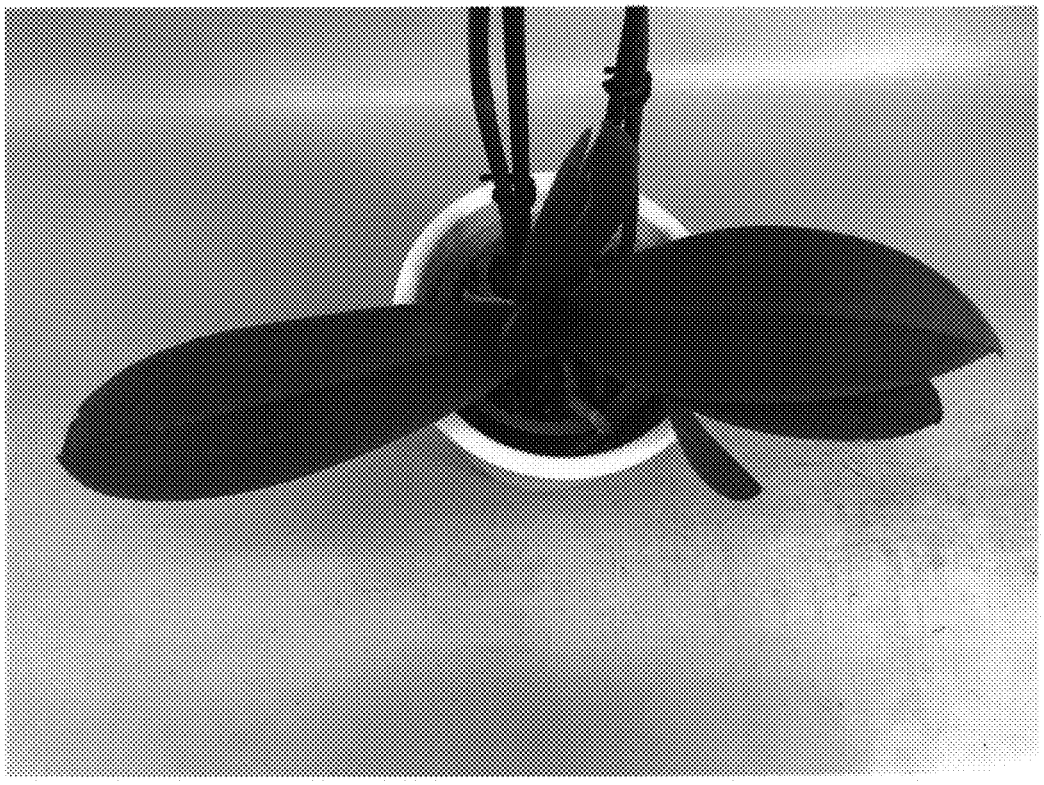
FIG. 3 shows an overhead view of the leaves of 'PHALARALS'.

The following detailed description sets forth the distinctive characteristics of 'PHALARALS'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in October 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALARALS'.

Parentage:

*Female parent*.—*Phalaenopsis* cultivar 'PHALVAPYH' (U.S. Plant Pat. No. 31,052).

*Male parent*.—*Phalaenopsis* cultivar '35337-02' (unpatented).

Propagation:

*Type*.—Meristem tissue culture.

Roots:

*Root description*.—Greyed-green (something between RHS 190B and 190C) colored roots with branching lateral roots having yellow-green (RHS 146B) with a hint of purplish-red (something in between RHS N77A and N77B) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height* (*from soil level to top of inflorescence*).—Approximately 42.0 cm to 47.0 cm.

*Width* (*measured from leaf tips*).—About 32.0 cm to 34.0 cm.

*Vigor*.—Strong.

Leaves:

*Mature leaves*.—Quantity per plant: 7 to 8 leaves are produced before flowering. Length (fully expanded): 17.0 cm to 19.0 cm. Width: 5.5 cm to 6.5 cm. Position of the broadest part of the leaf: Toward apex. Shape: Oblong. Base shape: Moderately elongated. Apex: Unequal obtuse. Leaf blade angle with the petiole (measured from the horizontal position): Between 30 degrees and 40 degrees. Leaf margin: Entire. Color: Upper surface: RHS 147A. Lower surface: RHS 146B with a diluting purple margin (RHS N77A). Texture (both upper and lower surfaces): Smooth. Thickness: 2.2 mm to 2.5 mm. Variegation: Absent. Venation: Pattern: Parallel. Color of the midvein: Upper surface: RHS 147A. Lower surface: RHS 146A.

Peduncle:

*Quantity per plant*.—1 to 2.

*Number of flowers per peduncle*.—10 to 14.

*Length*.—42.0 cm to 47.0 cm.

*Diameter*.—5.1 mm to 5.5 mm.

*Strength*.—Strong.

*Aspect*.—Upright to slightly pendent.

*Texture*.—Smooth.

*Color*.—Mix of dark reddish-brown (RHS 200A) and yellow-green (RHS 146C).

*Internode length*.—2.0 cm to 3.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 180.0 mm to 230.0 mm.

*Flowering time*.—First flowers can be expected 10 to 11 months after planting in a 12-cm pot.

*Flower*.—Height: 77.0 mm to 82.0 mm. Diameter: 90.0 mm to 95.0 mm. Depth of lip: 24.0 mm to 26.0 mm.

*Flower longevity*.—On the plant: 8 to 10 weeks.

*Flower shape in lateral view*.—Concave.

*Fragrance*.—Absent.

*Flower bud*.—Average size: Large. Length: 23.0 mm to 25.0 mm. Width: 20.0 mm to 22.0 mm. Shape: Egg shaped. Color: Yellow-green (RHS 144C) at the base; purplish-red (RHS N77B) with a touch of dark red (RHS 187C) toward the tip.

*Petals*.—Arrangement: Open/free. Shape: Semi-circular. Apex: Emarginated asymmetric. Margin: Weakly undulated. Length (from base to tip): 43.0 mm to 45.0 mm. Width: 54.0 mm to 56.0 mm. Position of the broadest part of the petal: Toward the base. Color (when fully opened): Upper surface: Basic color: Light reddish-purple (RHS N78D). Over color: White (RHS NN155C) at the base and purplish-pink shade (RHS N78C); reddish-purple midvein (RHS N78A). Lower surface: Basic color: Light purple (something in between RHS 76A and 76B). Over color: Hint of white (RHS NN155C) at the base and purplish-pink shade (RHS N78C). Number of spots and stripes on the petals (upper surface): Few stripes. Color of spots and stripes on the petals (upper surface): RHS N78B. Density of netting of the petals (upper surface): None. Color of the netting (upper surface): Not applicable.

*Dorsal sepal*.—Shape: Elliptic. Apex: Slightly emarginated symmetric. Margin: Entire. Length (from base to tip): 45.0 mm to 47.0 mm. Width: 31.0 mm to 33.0 mm. Position of the broadest part of the dorsal sepals: At the middle. Color (when fully opened): Upper surface: Basic color: Light reddish-purple (RHS N78D). Over color: White (RHS NN155C) at the base; purplish-pink shade (RHS N78C) toward margin on sides. Lower surface: Basic color: Light reddish-purple (RHS N78D). Over color: Light yellow-green (RHS 145C). Number of spots and stripes on the dorsal sepals (upper surface):

None. Color of spots and stripes on the dorsal sepals (upper surface): Not applicable. Density of netting of the dorsal sepals (upper surface): None. Color of the netting: Not applicable.

*Lateral sepals*.—Shape: Ovate. Apex: Obtuse symmetric. Margin: Entire. Length (from base to tip): 49.0 mm to 51.0 mm. Width: 29.0 mm to 31.0 mm. Position of the broadest part of the lateral sepals: At the base. Color (when fully opened): Upper surface: Basic color: Purplish-pink (RHS N78C). Over color: Small purplish-red region (RHS 185C) at the base and light yellow-green (RHS 145C) at the middle from the base toward tip. Lower surface: Basic color: Purplish-pink (RHS N78C). Over color: Light yellow-green (RHS 145C); few purplish-red stripes and midvein (RHS 61A). Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Whiskers: Present. Length of whiskers: 15.0 mm to 17.0 mm. Color of whiskers: White (RHS NN155C) at the base; light greenish-yellow (RHS 8B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 21.0 mm to 23.0 mm. Width: 16.0 mm to 18.0 mm. Color: Upper surface: Greenish-yellow (RHS 9D) at the base and yellow (RHS 9B) on one side; red-orange stripes (something in between RHS 178A and 178B) at the base; white (RHS NN155C) toward the tip with a touch of very light purple (RHS 76B). Lower surface: Touch of purplish-pink (RHS N78C) at the base toward margin; yellow on one side and touch of yellow (RHS 9B) on other side; white (RHS NN155C) toward the tip with a touch of very light purple (RHS 76B). Number of spots and stripes on the lateral lobe: Medium stripes at the base. Color of spots and stripes on the lateral lobe: Reddish-orange (something in between RHS 178A and 178B). Density of netting of the lateral lobe: None. Color of the netting: Not applicable.

*Apical lobe*.—Shape: Triangular. Margin: Entire. Length: 21.0 mm to 23.0 mm. Width: 23.0 mm to 25.0 mm. Color: Upper surface: Purplish-red margin (RHS 59B) at the base; greenish-yellow (RHS 7C) at the base and toward wings; white (RHS NN155C) toward whiskers. Lower surface: Purplish-red margin (RHS 59B) at the base; greenish-yellow wings (RHS 7C); reddish-purple (RHS N78B) toward whiskers. Number of spots and stripes on the apical lobe: None. Color of spots and stripes on the apical lobe: Not applicable. Density of netting of the apical lobe: None. Color of the netting: None.

*Callus*.—Average size: Medium to large. Height: 7.0 mm to 8.0 mm. Length: 5.0 mm to 6.0 mm. Width: 4.0 mm to 5.0 mm. Color: Yellow (RHS 9A); dotted (RHS 178A).

Reproductive organs:

*Column*.—Length: 8.0 mm to 10.0 mm. Diameter: 5.0 mm to 6.0 mm. Color: White (RHS NN155C) with very light purple tip (RHS 76B).

*Pollinia*.—Quantity: 2. Diameter: 0.8 mm to 1.0 mm. Color: Orange (RHS 25A).

*Ovary*.—Length: 7.0 mm to 9.0 mm. Diameter: 2.4 mm to 2.7 mm.

*Pedicel*.—Length: 30.0 mm to 32.0 mm. Diameter: 3.0 mm to 3.3 mm. Texture: Smooth. Color: Hint of brown (RHS 200C) at the base; light yellow-green (RHS 145C) with a touch of purplish-red (RHS N77D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALARALS' differs from the female parent plant 'PHALVAPYH' (U.S. Plant Pat. No. 31,052), in that 'PHALARALS' has a weak curvature of the lateral lobe, whereas 'PHALVAPYH' has a medium curvature of the lateral lobe. Additionally, 'PHALARALS' has longer whiskers than 'PHALVAPYH'.

'PHALARALS' differs from the male parent plant '35337-02' (unpatented) in that 'PHALARALS' has emarginated petal apexes, whereas '35337-02' has obtuse petal apexes. Additionally, 'PHALARALS' has smaller flowers than '35337-02'.

'PHALARALS' is most similar to the commercial *Phalaenopsis* plants named 'PHALMACHE' (unpatented) and 'PHALGORYQ' (U.S. Plant Pat. No. 31,050). 'PHALARALS' differs from the commercial variety 'PHALMACHE' in that 'PHALARALS' has slightly emarginated dorsal sepal apexes and a weak curvature of the lateral lobe, whereas 'PHALMACHE' has obtuse dorsal sepal apexes and a medium curvature of the lateral lobe. Additionally, 'PHALARALS' has smaller flowers than 'PHALMACHE'.

'PHALARALS' differs from the commercial variety 'PHALGORYQ' in that 'PHALARALS' has white columns with very light purple tips and a weak curvature of the lateral lobe, whereas 'PHALGORYQ' has very light purple columns with a light purple stripe in the middle and a strong curvature of the lateral lobe. Additionally, 'PHALARALS' has smaller flowers than 'PHALGORYQ'.

I claim:

1. A new and distinct variety of *Phalaenopsis* plant named 'PHALARALS', substantially as described and illustrated herein.

* * * * *